United States Patent [19]
Miura et al.

[11] Patent Number: 5,759,489
[45] Date of Patent: Jun. 2, 1998

[54] WASHING AND DISINFECTING METHOD AND APPARATUS FOR ARTIFICIAL DIALYZER USING ACID WATER ELECTROLYTICALLY MADE

[75] Inventors: Toshiyuki Miura, 12-2, Kidoguchi, Kisakata-machi, Yuri-gun, Akita-ken; Tetsurou Miura, Akita-ken, both of Japan

[73] Assignees: Miura-denshi Kabushiki-kaisha; Toshiyuki Miura, both of Akita-ken; Kouken Kabushiki-kaisha, Tokyo, all of Japan

[21] Appl. No.: 587,475

[22] Filed: Jan. 17, 1996

[30] Foreign Application Priority Data

| Jan. 17, 1995 | [JP] | Japan | 7-022268 |
| Dec. 1, 1995 | [JP] | Japan | 7-337862 |

[51] Int. Cl.⁶ ........................... A61L 2/02
[52] U.S. Cl. ................ 422/28; 134/22.11; 205/505; 205/626; 205/746; 210/636; 210/748
[58] Field of Search ............... 210/636, 748; 204/242, 252, 261, 273, 275; 205/746, 500, 626; 422/28

[56] References Cited

U.S. PATENT DOCUMENTS

| 4,166,031 | 8/1979 | Hardy | 210/636 |
| 4,695,385 | 9/1987 | Boag | 210/636 |
| 5,078,967 | 1/1992 | Riera Aixala | 422/28 |
| 5,234,563 | 8/1993 | Arai et al. | 204/263 |
| 5,256,371 | 10/1993 | Pippert | 210/636 |
| 5,268,144 | 12/1993 | Heilmann | 210/636 |
| 5,445,722 | 8/1995 | Yamaguti et al. | 204/263 |
| 5,474,662 | 12/1995 | Miyamae | 204/263 |
| 5,484,397 | 1/1996 | Twardowski | 210/636 |

FOREIGN PATENT DOCUMENTS

| 0737482 | 10/1996 | European Pat. Off. |
| 8-196625 | 8/1996 | Japan |

Primary Examiner—Peter A. Hruskoci
Assistant Examiner—Betsey J. Morrison
Attorney, Agent, or Firm—Oblon, Spivak, McClelland, Maier & Neustadt, P.C.

[57] ABSTRACT

An acid water obtain by electrolysis is used for wash disinfection inside as artificial dialyzer, thereby completely eliminating the bacteria, fungi, viruses, and other deposits inside the dialyzer.

13 Claims, 7 Drawing Sheets

WASHING AND DISINFECTING METHOD AND APPARATUS FOR ARTIFICIAL DIALYZER USING ACID WATER ELECTROLYTICALLY MADE

BACKGROUND OF THE INVENTION

1. Field of the Invention

The present invention relates to a washing and disinfecting method and apparatus for artificial dialyzer used for patients suffering from renal disease.

2. Related Background Art

Artificial dialysis is used to artificially purify the blood, which is guided out of a patient suffering from renal disease, by means of an artificial dialyzer. For example, an apparatus is arranged to introduce a solution A of a raw solution for dialysis composed mainly of a potassium chloride solution, a sodium chloride solution, or the like, a solution B of a sodium bicarbonate solution, and a clean water (a water let to pass through a reverse osmotic membrane to remove various germs, which is hereinafter sometimes referred to as "RO water") thereinto, as shore in FIG. 3. Then, the solution A, solution B, and clean water are mixed at the ratio of 1:2:32, thereby preparing a dialyzing fluid. After a concentration of the dialyzing fluid is checked, it is once stored in a reservoir. After the concentration of the dialyzing fluid is again checked, it is fed to each console, with which a patient is subjected to dialysis treatment. Each console uses the dialyzing fluid to continuously dialyze the blood of patient while continuously washing the reverse osmotic membrane (located outside the drawing).

Figure 3:
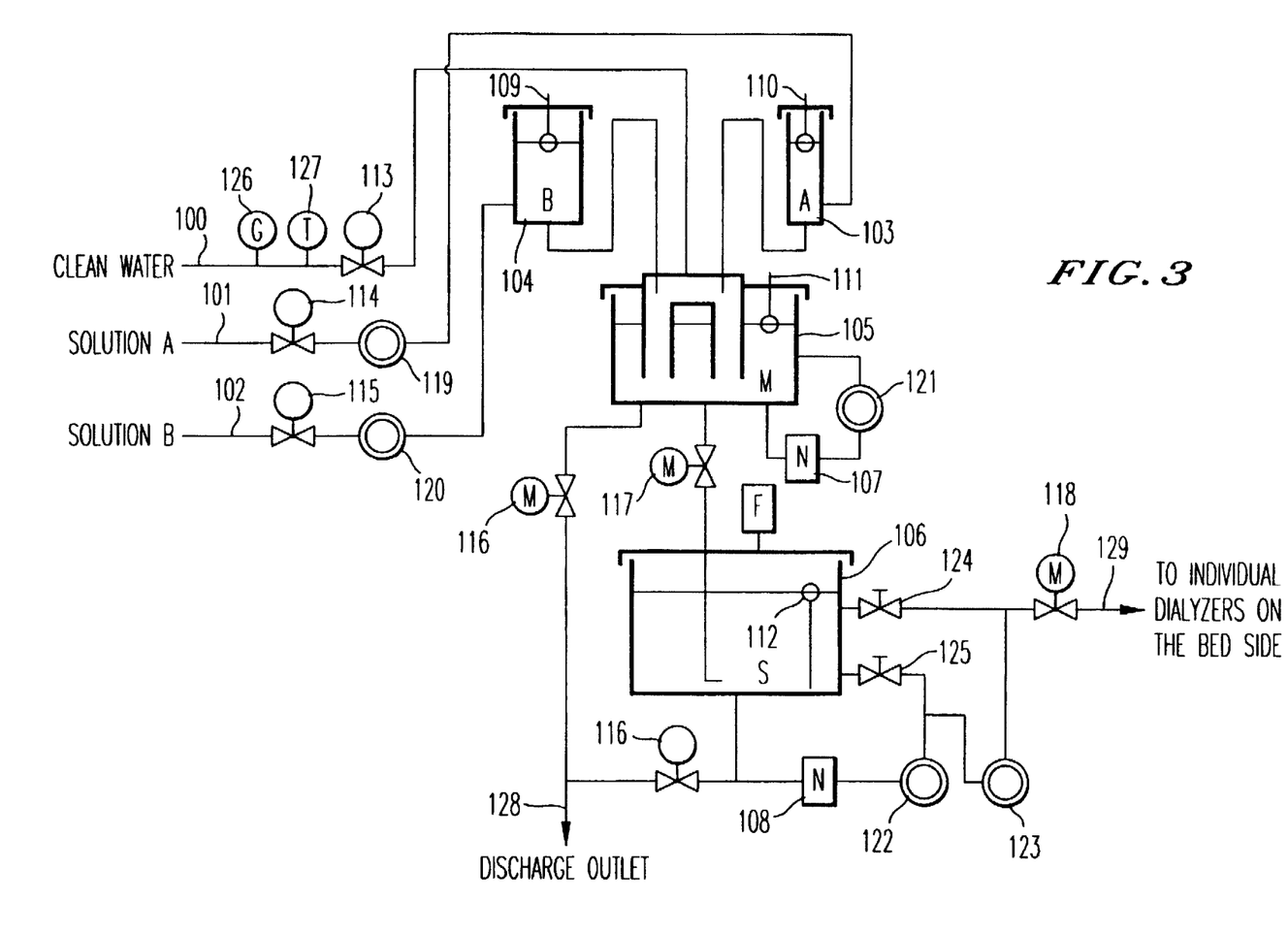
FIG. 3 is a schematic drawing to show a setup of an artificial dialyzing apparatus.

In FIG. 3, reference numeral 100 designates an inlet for clean water (RO water), 101 an inlet for solution A, 102 an inlet for solution B, 103 a measuring cup for solution A, 104 a measuring cup for solution B, 105 a mixing tank, 106 a reservoir, 107, 108 concentration meters, 109–112 float switches mounted on associated cups or tanks, 113, 114, and 130 electromagnetic valves, 116–118 motor-operated valves, 119–123 pumps, and 124, 125 manual valves.

Further, reference numeral 126 designates a pressure gauge, and 127 a thermometer. The dialyzer is composed of separate parts, i.e. a central part for controlling mixing of the dialyzing fluid and feeding thereof, and a console box part, which is connected to the central part through pipe lines, for receiving supply of the dialyzing fluid from the central part and effecting dialysis of the patient's blood through the osmotic membrane.

The artificial dialyzer as described above is used to perform hemodialysis usually at a frequency of once a week to once every few weeks in accordance with the stage of disease of the patient. Further, since the artificial dialyzer requires a high-level control, it is a present status that a plurality of patients use a single dialyzing apparatus by turns. Namely, the patients suffering from renal disease individually go to the facilities named as a dialysis center equipped with a plurality of artificial dialyzers, and some patients use one artificial dialyzer by turns for prescribed hemodialysis.

Accordingly, sufficient attention must be paid to various infectious diseases which can be contracted through the apparatus for artificial dialysis. Heretofore, immediately after completion of the dialyzing operation, the dialyzing fluid is drained and post-washing is conducted with the clean water. After the clean water is drained, a disinfecting operation is conducted with a disinfectant, thereby preparing for the next dialyzing operation. Then, before conducting the next dialyzing operation, further pre-washing is conducted in order to prevent infection from occurring through the apparatus for dialysis. Thus, the dialyzer is kept carefully washed and disinfected.

Figure 4:
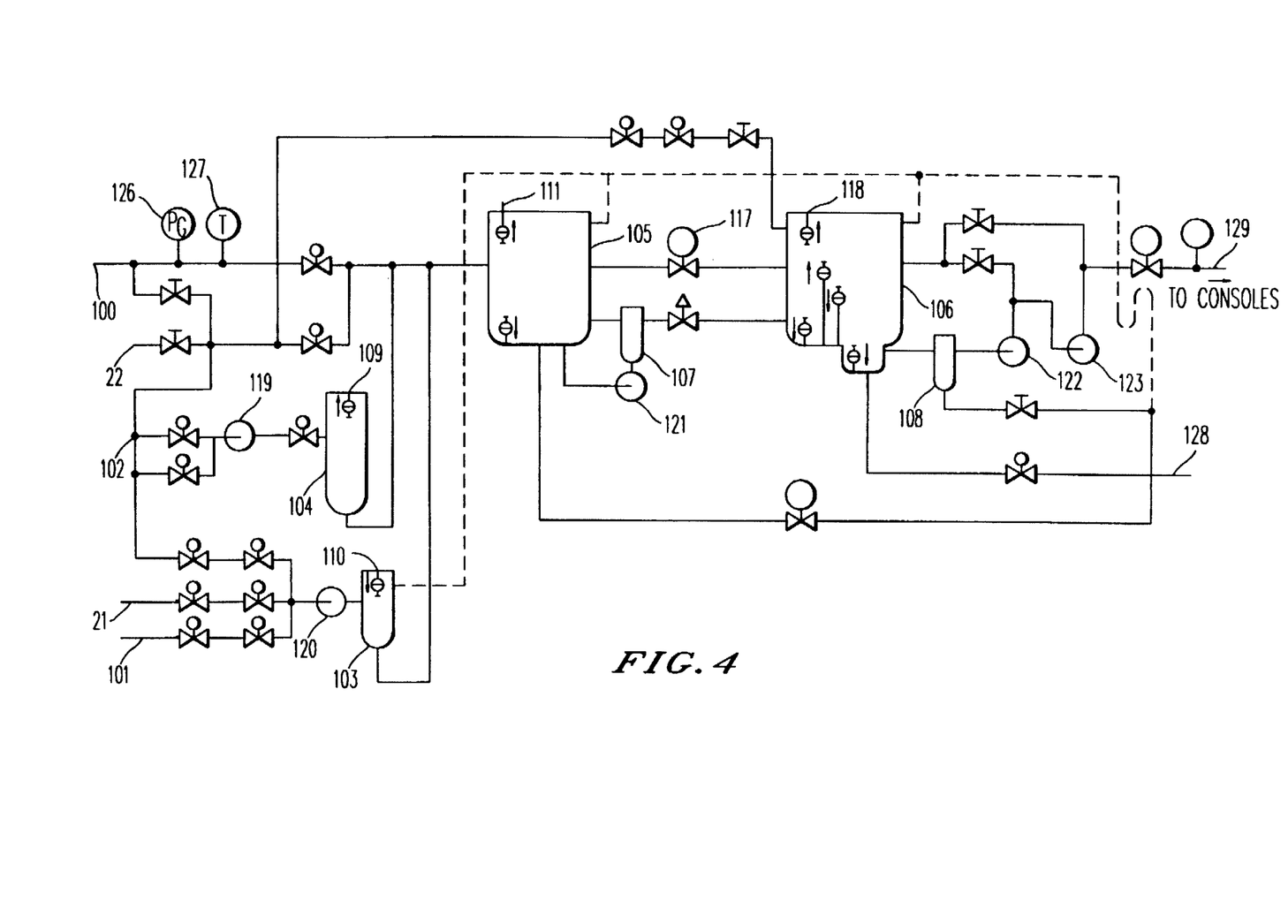
FIG. 4 is a drawing to show a component arrangement of the central part of the artificial dialyzing apparatus shown in FIG. 3.

Namely, as shown in FIG. 4, the conventional washing and disinfecting operation for dialyzer is conducted as follows. The clean water inlet (RO water inlet) 100, a boiling water inlet 22, the sodium bicarbonate solution inlet 102, a disinfectant inlet 21, and the raw solution inlet 101 are preliminarily connected to the apparatus. The dialyzing fluid stored in the mixing tank 105 and the reservoir 106 is drained by sequence control in a predetermined period. Then, hot water or boiling water is input into the apparatus and kept for several minutes, and the input hot water or boiling water is drained. After the washing operation, a disinfectant comprised of a sodium hypochlorite solution (0.01–0.02%) is introduced and retained until the next dialysis, thereby effecting wash and disinfection of the dialyzer comprised of the tanks, pipe lines, valves, etc.

Then, before the next dialysis operation, the disinfectant retained is drained, and thereafter the apparatus is filled with boiling water or hot water having passed through a reverse osmotic membrane for several minutes. Further, the clean water is introduced for several minutes to wash the apparatus, and then the dialyzing operation is conducted. Thus, every effort is made to prevent infection from occurring.

Furthermore, an acetic acid solution (0.1%) is poured into the apparatus once or twice a week to remove calcium, etc. adhering to the pipe lines, etc. In addition, a formalin solution is poured into the apparatus about once a month to perfect the disinfection.

FIG. 4 shows the flow of the medical fluid for washing and disinfecting the pipe line system including the mixing tank 105 and reservoir 106 when the disinfectant is injected and circulated. The clean water (RO water) and disinfectant each flow in the predetermined order at a predetermined interval through the tanks, the hemodialyzer portions having the osmotic membranes, and the pipe lines, thereby washing and disinfecting the tanks, the pipe lines, and the dialyzing portions of the osmotic membranes.

Figure 5:
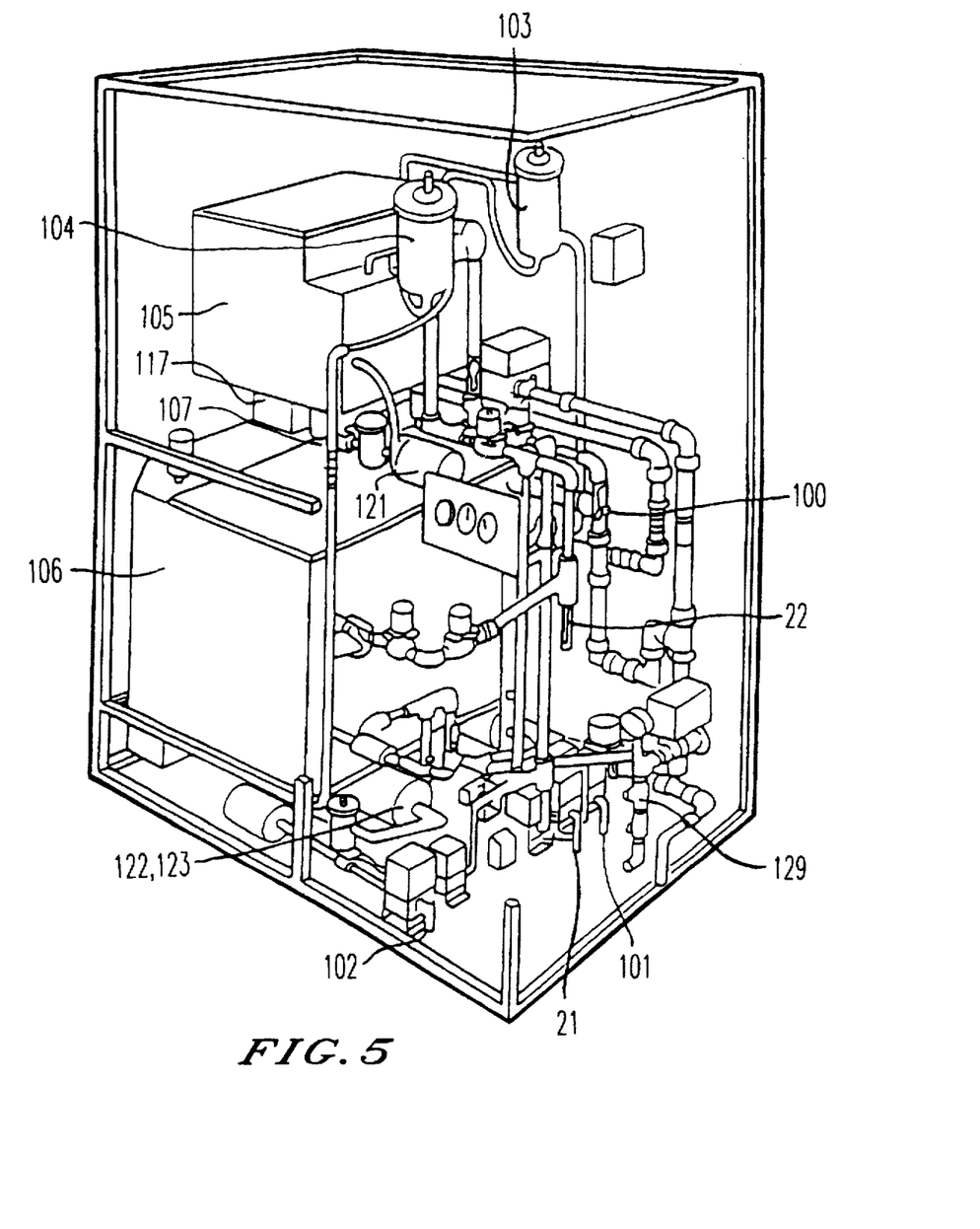
FIG. 5 is a drawing to show flow of the medical fluid for washing and disinfecting the pipe lines including mixing tank 105 and reservoir 106 by inputting and circulating the disinfectant.

Further, FIG. 5 is a schematic and perspective view to show the central part of the artificial dialyzer as described above. The same numbers in FIG. 5 as those in FIG. 3 and FIG. 4 denote the same portions as in FIG. 3 and FIG. 4. The apparatus of FIG. 5 is provided with the pipe lines, pumps, and valves for injecting, circulating, and retaining the washing solutions (the disinfectant, etc.) for washing and disinfecting the artificial dialyzer, similar to those shown in FIG. 4, in addition to the fundamental structure as shown in FIG. 3.

However, bacteria, fungi, viruses, etc. in the dialyzer were not able to be eliminated completely therefrom even by a long-term washing and disinfecting operation for one to three hours using the disinfectants mainly of the sodium hypochlorite solution and the acetic acid solution before and after dialysis, thus failing to completely suppress occurrence of infectious disease. Particularly, there were the following problems. A nutrition source, such as calcium, protein, etc. contained in a fine amount in the dialyzing fluid, the water, the blood, etc., adhered to the inside of the pipe lines, etc., and new various germs, etc. propagated there. There remained the toxins (enzymes) produced by the various germs, and dead bodies of bacteria per se (endotoxins) inside the pipe lines, and they were brought into the patient's body with return of the blood, which could cause the patient to have high fever.

Further, the wash and disinfection with sodium hypochlorite, etc. the adverse effects of the residual components on the human bodies and on the other environments would result after use for a long period. Furthermore, since sodium hypochlorite is alkaline, the disinfecting effect is low. Therefore, unless it were used in a concentration of about 1000 ppm, the disinfecting effect thereof would be weak. On the other hand, if it were used in such a high concentration, chlorine would remain 500 ppm or so in waste water. Therefore, the residual chlorine in the high concentration would cause serious environmental pollution. Accordingly, in order to prevent the environmental pollution, the facilities with the dialyzer need a waste water treatment for decreasing the residual chlorine of the high concentration, which forces enormous expense.

SUMMARY OF THE INVENTION

Under the circumstances as described above, an object of the present invention is to provide a method and apparatus by which the inside of the dialyzer can be washed and disinfected in a short period of time and with certainty and by which the nutrition source such as calcium, protein, etc. adhering to the inside of the pipe lines etc. can be certainly eliminated, thereby preventing intracorporeal pyrogenic substances such as endotoxins from intruding into the body through the dialyzing fluid.

To achieve the object, the present invention has established a method for washing and disinfecting the dialyzer in a short period of time and with certainty, and also for eliminating the dialyzing fluid adhering to the inside of the pipe lines, in which a water (tap water or RO water: water passing a reverse osmotic membrane), having an inorganic additive such as a salt or the like dissolved, is supplied to an electrolytic cell having an anode and a cathode and partitioned by a diaphragm between the anode and cathode, a direct current of a predetermined voltage is applied to the two electrodes to obtain an acid water containing at least 5 ppm of an oxidized or chlorinated substance such as $Cl_2$, HOCl, or $O_3$ and showing pH in the range of 3.2 to 2.0 both inclusive and an oxidation-reduction potential of at least 870 mV from the anode side, and the acid water is supplied to the disinfectant inlet 21, a clean water inlet (RO water inlet) 100, the solution-A inlet 101, or the solution-B inlet 102 of the dialyzer to wash and disinfect the inside of the dialyzer.

Further, the present invention has established a method for washing and disinfecting the dialyzer in a short period of time and with certainty, and also for eliminating the dialyzing fluid adhering to the inside of the pipe lines, in which a water, having an inorganic additive such as a salt or hydrochloric acid dissolved, is supplied to an electrolytic cell having an anode and a cathode but having no diaphragm, a direct current of a predetermined voltage is applied to the two electrodes to obtain an acid water containing at least 5 ppm of an oxidized or chlorinated substance such as $Cl_2$, HOCl, or $O_3$ and showing pH in the range of 6.5 to 2.0 both inclusive and an oxidation-reduction potential of at least 800 mV from the anode side, and the acid water is supplied to the disinfectant inlet 21 of the dialyzer to wash the inside of the dialyzer.

Furthermore, the present invention has established a method for washing and disinfecting the dialyzer in a short period of time and with certainty, and also for eliminating the dialyzing fluid adhering to the inside of the pipe lines, in which a water, having an inorganic additive such as a salt or hydrochloric acid dissolved, is supplied to an electrolytic cell having an anode and a cathode and partitioned by a diaphragm between the anode and cathode, a direct current of a predetermined voltage is applied to the two electrodes to obtain an acid water from the anode side, an inorganic acid such as hydrochloric acid or a halogenated substance such as sodium hypochlorite is mixed to the acid water to obtain a solution containing at least 5 ppm of an oxidized or chlorinated substance such as $Cl_2$, HOCl, or $O_3$ and showing pH in the range of 5.0 to 2.0 both inclusive and an oxidation-reduction potential of at least 800 mV, and the solution is supplied to the disinfectant inlet 21 of the dialyzer to wash and disinfect the inside of the dialyzer.

Since sodium hypochlorite having been used as a disinfectant has pH in the alkaline range and NaClO and ClO exist in the solution in the form of ions, its oxidizing power is weak, and disinfecting effect thereof is thus weak. Therefore, extremely excellent disinfection can be effected using the acid water made by electrolysis (electrolytic acid water) as a washing and disinfecting water instead of sodium hypochlorite because of the strong oxidizing power of the oxidized or chlorinated substance such as $Cl_2$, HOCl, $O_3$, or the like obtained by electrolysis.

Further, sodium hypochrolite had such problems that it remained inside the pipe lines in the form of a salt and that it was easily coupled with calcium in the dialyzing fluid to adhere to the inside of the pipe lines, where various germs would propagate. In contrast, the acid water obtained by electrolysis neither remains inside the pipe lines in the form of a salt, nor is coupled with calcium. Rather, it reacts with remaining protein or the like to decompose the protein per se. As a result, it can decompose and eliminate the deposits per se remaining inside the pipe lines and being composed of the protein.

Accordingly, the present invention can provide the washing and disinfecting method by which washing and disinfection can be effected in a short period of time and with certainty, and by which the dialyzing fluid adhering to the inside of the pipe lines can also be eliminated with use of the acid water containing the certain oxidized or chlorinated substance such as $Cl_2$, HOCl, $O_3$, or the like and showing a certain pH in the predetermined range and a predetermined oxidation-reduction potential as the washing and disinfecting water for dialyzer.

DESCRIPTION OF THE PREFERRED EMBODIMENTS

Embodiments of the present invention will be described with reference to the drawings.

Figure 1:
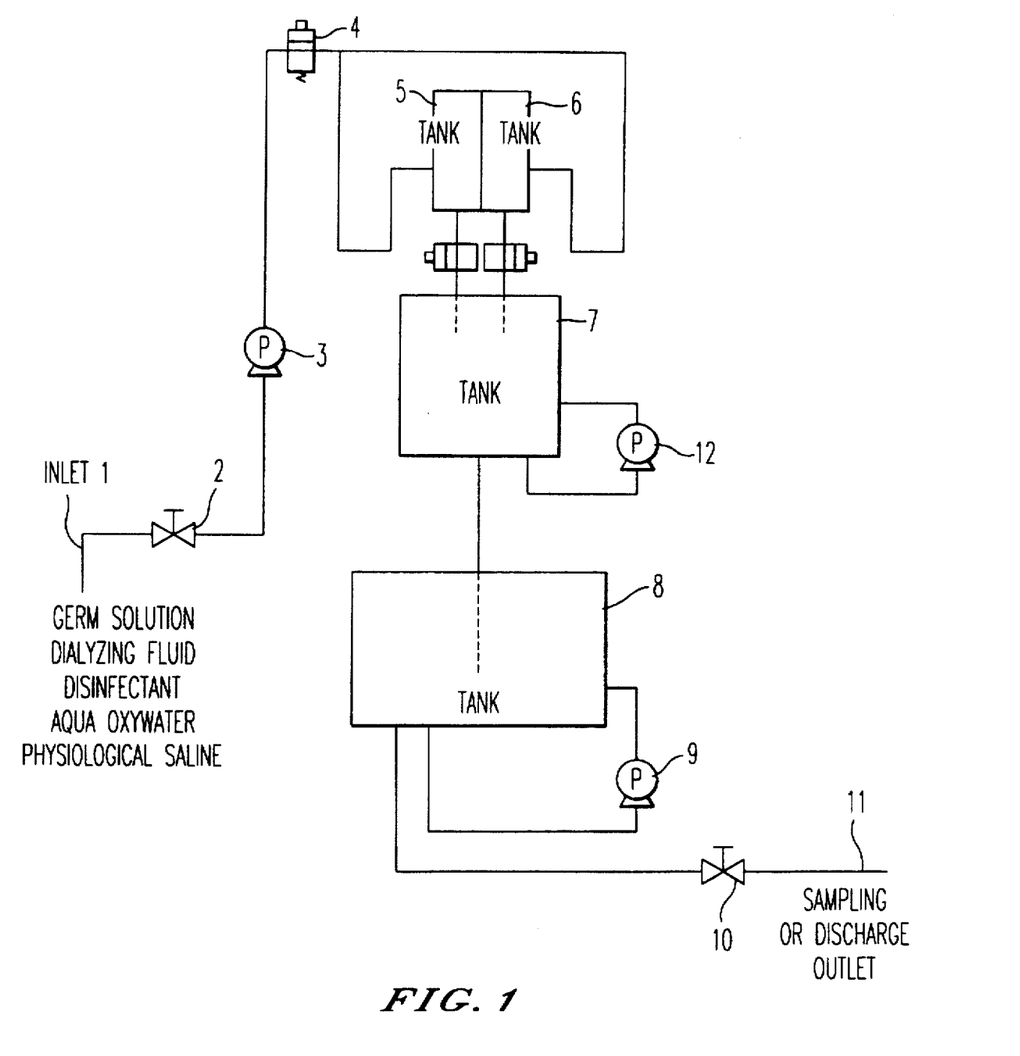
FIG. 1 is a schematic drawing to show a prototype model apparatus used in the first embodiment.

First of all, an embodiment of the present invention was arranged as regarding the dialyzer as a model apparatus comprised of tanks and pipe lines so as to permit a dialyzing fluid, a solution containing test germs, a reference disinfectant, AQUA OXYWATER (the electrolytic acid water available from Miura Denshi K.K.), or the like to be introduced thereinto and to be reserved therein. Comparison was made using the model apparatus between the effect of disinfection with sodium hypochlorite as the reference disinfectant and the effect of disinfection according to the present invention. FIG. 1 is a schematic drawing to show the prototype model apparatus used in the first embodiment.

In FIG. 1, reference numeral 1 designates an inlet through which the dialyzing fluid, solution of test germs, reference disinfectant, electrolytic acid water, or physiological saline can be input into the apparatus, 2 an electromagnetic control valve for controlling an input amount, 3 a pump for introducing the solution into a tank, 4 an electromagnetic valve for controlling introduction of solution, 5 a cup tank corresponding to the solution-B measuring cup 109 of the dialyzer described above, 6 a cup tank corresponding to the solution-A measuring cup 110 described above, 7 a tank corresponding to the mixing tank 105 described above, 8 a tank corresponding to the reservoir tank 106 described above, 9, 12 pumps for circulating the solution in the tanks 7, 8, respectively, 10 a discharge valve for controlling discharge of the solution stored in the tank 8, and 11 a sampling outlet from which a sample is taken out.

Each tank or valve was connected to an associated part with a silicone tube or a Teflon tube as previously shown in the scheme of the artificial dialyzer. Further, in addition to these tubes, a vinyl chloride tube and a polypropylene tube were used as other pipe lines in the model apparatus. Pipe lines made of a polypropylene are used in most actual dialyzers, and pipe lines made of a polyvinyl chloride are also used in some dialyzers. Therefore, the vinyl chloride tube was partially used in the model apparatus.

Two types of polypropylene tanks were used for the tanks. Tanks having the volume of two liters were used as the above measuring cup tanks, and tanks having the volume of ten liters as the mixing tank and the reservoir tank. Although the tanks were made of metals or plastics in the actual dialyzers, the polypropylene tanks were used in the present embodiment because of easiness to produce the prototype model apparatus.

Further, the valves (electromagnetic valves) for controlling the introduction amount and the pressure between the tanks were those actually used for dialyzers. Namely, the electromagnetic valves were made of stainless steel of SUS 316 in the portions in contact with the solution because the actual dialyzers employ non-rusting valves in order to avoid rust on parts. Furthermore, Teflon was used for the portions other than the portions in contact with the solution. Magnet pumps were used as the pumps, and polypropylene was used in the portions in contact with the solution.

Using the model apparatus, two types of washing and disinfecting conditions for dialyzer were set by the following steps and were compared with each other.

(a) First of all, various kinds of bacteria (Staphylococcus, *Escherichia coli, Pseudomonas aeruginosa*, fungus) were cultured and prepared at predetermined turbidity (10°) (Step 1).

(b) Next, the dialyzing fluid was supplied to the prototype model apparatus, thereby filling the inside of each tank 5, 6, 7, 8 with the dialyzing fluid. Then the pumps 9, 12 were operated for 60 minutes so that the dialyzing fluid was circulated in the prototype model apparatus, thereby making the dialysis operating conditions (Step 2).

(c) After that, the circulation by the pumps was stopped and the dialyzing fluid in the apparatus was drained (Step 3).

(d) Then, the germ solution prepared in Step 1 was supplied into the prototype model apparatus, and the germ solution was circulated for 20 minutes by operating the pumps as described above (Step 4).

(e) The germ solution was drained (Step 5).

(f) The apparatus was subjected to air-drying for 360 minutes (Step 6).

(g) A sodium hypochlorite solution (0.02%) was introduced into the apparatus (Step 7).

(h) The pumps were operated to wash the inside of the prototype model apparatus for ten minutes (Step 8).

(i) Clean water passing through a reverse osmotic membrane (RO water) was supplied and circulated for ten minutes as above, and was then drained (Step 9).

(j) Physiological saline was supplied to fill in the inside of the prototype model apparatus, and then the germs were collected (Step 10).

(k) After the germs collected were put on various agar culture media and cultured at 37° C. for 24 hours, colonies were counted (Step 11).

(l) After repeating above Step 1 to Step 6 next day, an acid water having properties of pH of 2.6, an oxidation-reduction potential of 1083 mV, and a residual chlorine concentration of 25 ppm (the acid water available from Miura Denshi K.K., trade name "AQUA OXYWATER") was introduced into the prototype model apparatus and was circulated for ten minutes for washing. Then the solution was drained (Step 12).

(m) The number of bacteria was counted after above Steps 10 and 11 (Step 13).

The present embodiment used the following agar culture media; a nutrient (HI) agar culture medium for detecting general bacteria, a mannitol salt (MS) agar culture medium for detecting Staphylococcus, an NAC agar culture medium for detecting Pseudomonas aeruginosa, a Desoxycholate (DOC) agar culture medium for detecting *Escherichia coli*, and a Sabourand's glucose agar culture medium for detecting the fungus (Candida). Further, the test bacteria to be introduced were S. aureus (*Staphylococcus aureus*), E. coli (*Escherichia coli*), P. aeruginosa (*Pseudomonas aeruginosa*), and Candida albicans (Candida fungus).

The acid water of the present invention was compared with the reference disinfectant as follows.

They were compared with respect to decreased numbers in of bacteria before and after the treatment. The results thus obtained are shown in Table 1. Here, in either case, three samples were taken to calculate a mean value. The mean values thereof were compared.

TABLE 1

| Kind of Bacteria | Sodium Hypochlorite | AQUA OXYWATER |
|---|---|---|
| S. aureus | $0.8 \times 10$ | Negative |
| E. coli | Negative | Negative |
| P. aeruginosa | $2.3 \times 10^2$ | Negative |

TABLE 1-continued

| Kind of Bacteria | Sodium Hypochlorite | AQUA OXYWATER |
|---|---|---|
| *Candita albicans* | 8.2 × 10 | Negative |
| General bacteria | 2.6 × 10 | Negative |

As seen from Table 1, after the treatment with the acid water obtained by electrolysis ("AQUA OXYWATER"), the detection results of S. aureus, E. coli, P. aeruginosa, and Candida albicans were all negative, and the detection result of the general bacteria was also negative.

Next, an actual dialyzer was used to compare the washing and disinfecting effects. AQUA OXYWATER (the electrolytic acid water available from Miura Denshi K.K.) was introduced into the inlet for introducing sodium hypochlorite, and the washing and disinfecting effect thereof was compared with that when the dialyzer was washed and disinfected with the sodium hypochlorite solution.

Figure 2:
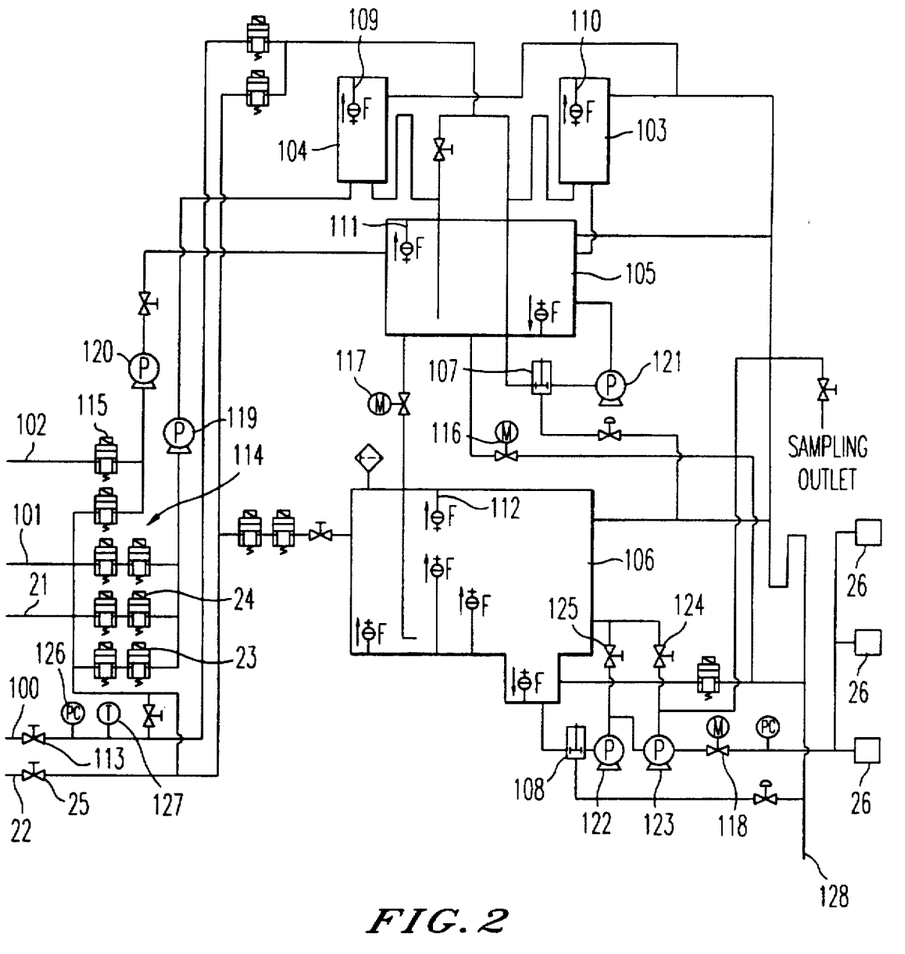
FIG. 2 is a schematic drawing to show an example of disinfecting an actual dialyzing apparatus with AQUA OXY-WATER (the electrolytic acid water available from Miura Denshi K.K.)

FIG. 2 is a schematic drawing to show an apparatus for washing and disinfecting the actual dialyzer with AQUA OXYWATER (the electrolytic acid water available from Miura Denshi K.K.), in which the dialyzer is fundamentally the same as the one shown in FIG. 3 to FIG. 5.

For convenience's sake of explanation, reference numerals for respective parts are the same as those in FIG. 3 to FIG. 5. However, this apparatus is different only in the following point from the apparatus in FIG. 3 to FIG. 5. In order to automatize the disinfecting operation of dialyzer, the apparatus of this embodiment is provided with a disinfectant inlet for introducing the sodium hypochlorite solution as a disinfectant (which was described as the disinfectant inlet 21 in the above description, and which is the same inlet) into the apparatus and a boiling water inlet 22 for introducing boiling water to disinfect the apparatus therewith, as the apparatus shown in FIG. 4 is, in addition to the dialyzing fluid inlet and the clear water inlet. Further, with addition of the inlets, the inlets 21, 22 were provided with electromagnetic valves 23, 24 and a manual valve 25 for controlling the introduction of solution, respectively.

In the present embodiment, AQUA OXYWATER (the electrolytic acid water available from Miura Denshi K.K.) was introduced through the disinfectant inlet 21, instead of the sodium hypochlorite solution conventionally introduced for disinfection, thereby washing and disinfecting the dialyzer. When AQUA OXYWATER was introduced through the disinfectant inlet 21, a sequencer was operated so that AQUA OXYWATER might not be diluted; otherwise, the disinfectant would be usually diluted with clean water on an automatic basis. Then, the results were compared with the results in the case of conventional disinfection with sodium hypochlorite.

For the comparison, first, a number of residual bacteria was checked when the dialyzer was washed and disinfected with the sodium hypochlorite solution (100 ppm) conventionally used. Namely, (1) washing was conducted with RO water (the water through the reverse osmotic membrane) for 60 minutes after dialysis, (2) disinfection was conducted for 40 minutes with the sodium hypochlorite solution, (3) the sodium hypochlorite solution was retained for eight hours as it was, (4) washing was conducted with RO water for 60 minutes before start of next dialysis, (5) a test solution was sampled from a plurality of console boxes (the treatment facilities having beds on which the patients were treated by the dialyzer), and (6) the solution sampled was cultured at 37° C. for 24 hours.

Namely, a number of residual bacteria under the actual dialyzing conditions can be obtained by checking the number of residual bacteria in the RO water before start of next dialysis. Here, in sampling the test solution from the console boxes, a solution was sampled from the console box located at the farthest distance from the main unit among the three console boxes because the box at the farthest distance was considered to show the worst washing effect. The solution was cultured.

Further, this test was repeated every day from a Monday to the next Monday except for Sunday as sampling the test solution. Furthermore, on Wednesday and Saturday and before the washing and disinfecting operation with sodium hypochlorite, washing with acetic acid (0.1%) was conducted for 40 minutes to remove calcium, etc. adhering to the inside of the pipe lines.

The results are shown in Table 2.

It is seen from Table 2 that residual bacteria were detected in the samples after culturing of the solutions sampled from the console box, which means that the above washing and disinfecting operation with sodium hypochlorite was not complete.

Next, the dialyzer was washed with AQUA OXYWATER (the electrolytic acid water available from Miura Denshi K.K.) as the embodiment of the present invention and the number of bacteria was checked.

In this case, the dialyzer was washed as follows.

TABLE 2

| Test No. | Name of Bacteria Detected | Number of Bacteria |
|---|---|---|
| 1 | *Pseudomonas sp* | $3.2 \times 10^3$ |
|  | *Pseudomonas aeruginosa* | $1.3 \times 10$ |
| 2 | *Bacillus sp* | $8.1 \times 10$ |
|  | *Pseudomonas sp* | $1.5 \times 10$ |
| 3 | *Alcaligenes faecalis* | $1.8 \times 10^2$ |
|  | *Pseudomonas sp* | $5.5 \times 10$ |
| 4 | *Staphylococcus sp* | $6.3 \times 10^2$ |
| 5 | *Pseudomonas sp* | $3.1 \times 10^4$ |
| 6 | *Pseudomonas sp* | $8.2 \times 10^3$ |
|  | *Seratia sp* | $1.8 \times 10$ |
| 7 | *Corynebacterium sp* | $6.4 \times 10^2$ |

(1) Washing was conducted for 30 minutes with RO water (the water through the reverse osmotic membrane) after dialysis, (2) washing was conducted for 20 minutes with AQUA OXYWATER (the electrolytic acid water : pH 2.5; the oxidation-reduction potential 1150 mV; the residual chlorine concentration 25 ppm), (3) the AQUA OXYWATER was retained for eight hours as it was, (4) washing was conducted for 30 minutes with RO water before start of next dialysis, (5) a test solution was sampled from the console box located at the farthest distance, and (6) the solution sampled was cultured at 37 ° C. for 24 hours. Namely, a number of residual bacteria can be obtained under the actual dialyzing conditions by checking the number of residual bacteria in the RO water before start of next dialysis, as in the previous case.

The results are shown in Table 3. Also, in the present embodiment, the bacteria test was repeated from a Monday to the next Monday except for Sunday as in the previous case.

It is clear from Table 3 that Pseudomonas sp was slightly detected in the test sample on the first day, the first Monday. However, the test samples on the other days were all negative, and no bacteria were thus detected. It

TABLE 3

| Test No. | Name of Bacteria Detected | Number of Bacteria |
| --- | --- | --- |
| 1 | Pseudomonas sp | 1.2 × 10 |
| 2 | Negative | 0 |
| 3 | Negative | 0 |
| 4 | Negative | 0 |
| 5 | Negative | 0 |
| 6 | Negative | 0 |
| 7 | Negative | 0 |

TABLE 4

| | Changes of Calcium (Ca) Concentration in Use of Acid | | | | |
| --- | --- | --- | --- | --- | --- |
| | At Prewashing with Water | At Washing with Acid Water | At Second Prewashing with Water | At Second Washing with Acid Water | At Third Prewashing with Water |
| Central Part | 0.5 mg/dl | 0.7 mg/dl | 0.1 mg/dl | 0 | 0.1 mg or less |
| CONSOLE 1 | 0.8 mg/dl | 3.5 mg/dl | 0.2 mg/dl | 0 | 0.1 mg or less |
| CONSOLE 2 | 1.6 mg/dl | 4.3 mg/dl | 0.2 mg/dl | 0 | 0.1 mg or less |
| CONSOLE 3 | 3.1 mg/dl | 5.8 mg/dl | 0.3 mg/dl | 0 | 0.1 mg or less | is understood that bacteria, which could not be removed with AQUA OXYWATER, were detected on the first day, but the bacteria were completely removed by AQUA OXYWATER after that. It is presumed that the bacteria detected on the first day were those dissolving into the solution out of the deposits adhering to the inside of the pipe lines in the conventional method.

In the washing operation with the sodium hypochlorite solution, washing with acetic acid (0.1%) for 40 minutes was conducted before the washing and disinfecting operation with sodium hypochlorite on Wednesday and Saturday, thereby removing calcium, etc. adhering to the inside of the pipe lines. On the other hand, in the washing operation with AQUA OXYWATER, the deposits containing calcium etc. adhering to the inside of the pipe lines can be decomposed and removed by AQUA OXYWATER. In order to show the effect, concentrations of residual calcium were measured separately. A measuring method was as follows. Namely, the residual calcium concentrations were measured five times, at prewashing with water, at washing with AQUA OXYWATER, at second prewashing with water, at second washing with AQUA OXYWATER, and at third prewashing with water in this order. The residual calcium concentrations were measured at four places, i.e. the central part, console box $26_1$, console box $26_2$, and console box $26_3$ of the dialyzer.

The results are shown in Table 4.

It is clear from Table 4 that the residual calcium is detected at the first prewashing with water, and the concentration thereof increases at the successive washing with AQUA OXYWATER. It is considered that the reason is that the calcium component adhering and depositing on the inside of the pipe lines was dissolved by AQUA OXYWATER, whereby the residual component temporarily increased. However, after that, the residual calcium component was completely removed and no residual calcium component was detected at the second washing with AQUA OXYWATER.

A slight amount of the calcium component was detected at the final washing with water (at the third prewashing with water), the reason of which is considered to be that the calcium component contained in the RO water per se was detected.

Here, the residual calcium component was detected in accordance with the EDTA titration method.

Next, the dialyzer was washed with AQUA OXYWATER, and removal of endotoxins was verified as the third embodiment.

The washing method of this case was as follows.

(1) An AQUA OXYWATER maker (trade name "OXYLYZER": available from Miura Denshi K.K.) was operated to obtain an acid water having pH of 2.5 or less.

(2) AQUA OXYWATER (acid water) was stored in a reservoir of OXYLYZER.

(3) After completion of dialysis, postwashing was conducted for at least 30 minutes with RO water, thereby washing the tanks and pipe lines inside the central part of dialyzer, and the pipe lines inside the consoles.

(4) AQUA OXYWATER was supplied from reservoir of OXYLYZER to the disinfectant inlet 21 of the dialyzer. Instead thereof, AQUA OXYWATER may be supplied directly to the reservoir tank 106 of the dialyzer from the reservoir of OXYLYZER, or through the boiling water inlet 22.

(5) Washing with AQUA OXYWATER was conducted for at least 15 minutes, thereby sufficiently washing the pipe lines of dialyzer and the pipe lines to the consoles.

(6) AQUA OXYWATER was retained for at least 20 minutes in such a state that AQUA OXYWATER remained in the reservoir tank 106 (AQUA OXYWATER was retained also in the pipe lines in the consoles accordingly).

(7) Just before start of dialysis, prewashing was conducted (for 30 or more minutes) with the RO water, and then RO water was discharged (or drained).

(8) Dialysis was started.

After completion of the dialyzing operation as above, endotoxins were measured. The results thus obtained were compared with those obtained in the case where washing and disinfection was effected using the conventional sodium hypochlorite solution. Endotoxins were measured by means of a commercially available measurement kit from K.K. Sesikagaku Kogyo and an amount thereof was measured.

The results showed that the endotoxins existed in the solution in the amount of 582.06 in the central part and in the amount of 416.04 in the console part (console box $26_3$) (in the units of Eu/l in either case) in the case of washing with the conventional sodium hypochlorite solution. On the other hand, the amounts of the endotoxins remarkably decreased to 2.21 to 1 (Eu/l) or less in the central part and 11.51 to 1 (Eu/l) or less in the console part (console box 26₃) in the case of washing with AQUA OXYWATER.

This confirmed that the washing of dialyzer with AQUA OXYWATER had not only a superior disinfecting ability to that of the conventional washing with the sodium hypochlorite solution, but also an extremely superior effect to remove the endotoxins, which could not be obtained in the conventional washing with the sodium hypochlorite solution.

Next described is a modification of the washing and disinfecting method for artificial dialyzer using the electrolytic acid water according to the present invention. Before circulating and retaining the acid water in the dialyzer, an alkaline water obtained by electrolysis was introduced through the disinfectant inlet 21 into the artificial dialyzer, and it was circulated and retained for a predetermined period in the artificial dialyzer. Thereafter, the acid water (AQUA OXYWATER) having the predetermined pH and oxidation-reduction potential as described above was introduced through the disinfectant inlet 21 into the artificial dialyzer, and was circulated and retained for a predetermined period in the artificial dialyzer. Further, the acid water was an acid water containing a certain oxidized or chlorinated substance, which was introduced through the disinfectant inlet 21 into the artificial dialyzer and which was circulated and retained for a predetermined period in the artificial dialyzer.

The alkaline water used in this modification had pH of at least 9.0. If the alkaline water has pH of at least 9.0, it makes protein swollen upon contact therewith because of the hydroxyl ion therein, whereby the protein comes to be destroyed.

The above treatment can increase the ability to decompose the substances adhering to the inside of the pipe lines, which are composed mainly of protein, thus achieving more excellent removal of deposits. Accordingly, the deposits in the pipe lines can easily be removed by the treatment with the alkaline water before circulating and retaining the acid water. Thereafter, the washing and disinfection with acid water was conducted, thereby making the washing and disinfecting effect in the artificial dialyzer more excellent.

In the next place, the inventor of the present invention incorporated the above making apparatus for making the electrolytic acid water in an artificial dialyzing apparatus, thereby developing a washing and disinfecting apparatus for artificial dialyzer using the electrolytic acid water made by the making apparatus.

Figure 6:
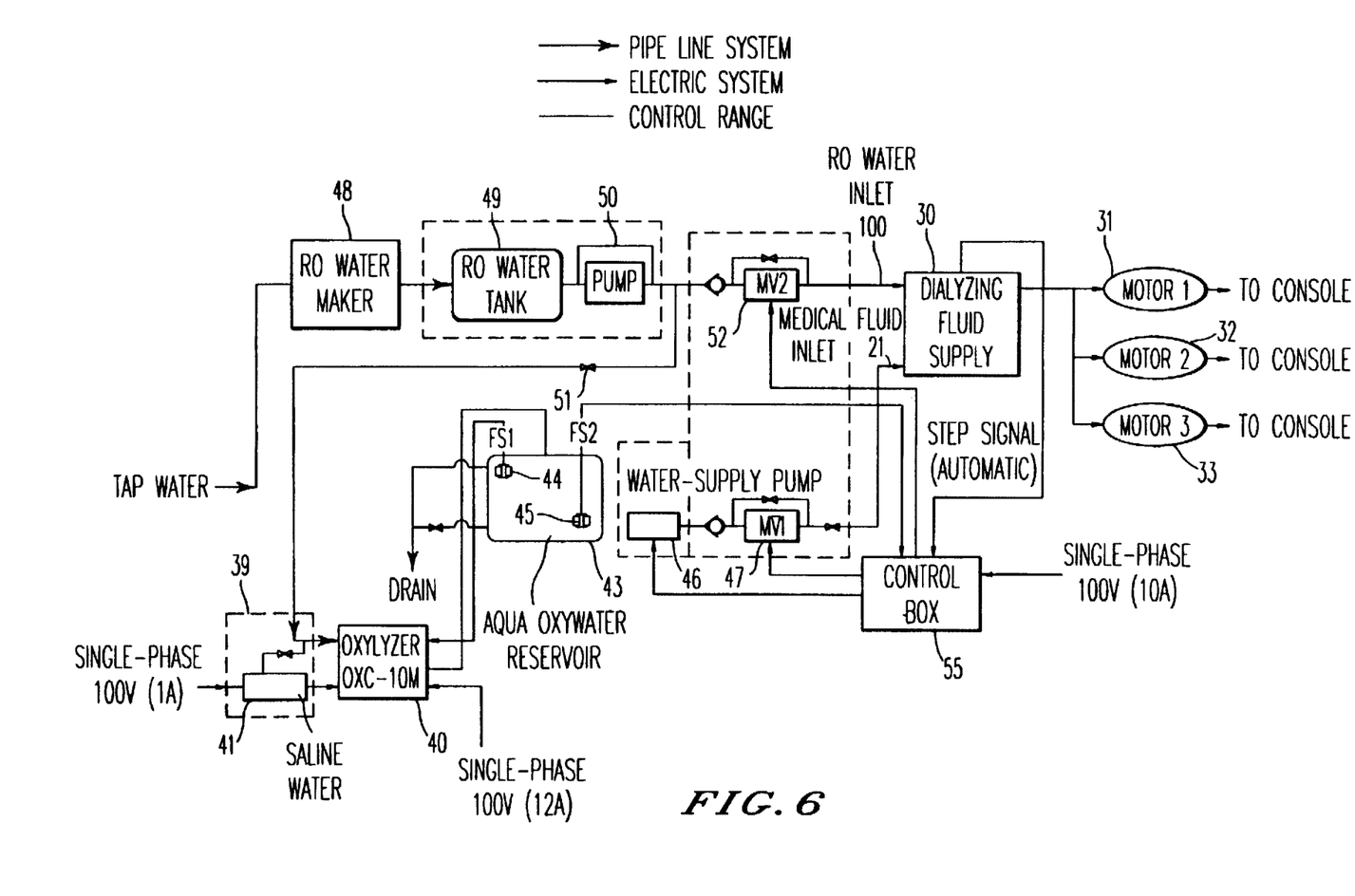
FIG. 6 is a schematic drawing to show an embodiment of the washing and disinfecting apparatus for artificial dialyzer using the electrolytic acid water.

FIG. 6 is a schematic diagram to show an embodiment of the washing and disinfecting apparatus. In this embodiment, only the washing and disinfecting step will be explained as omitting the description of the A-solution inlet and B-solution inlet, and the same members as those in the description of the conventional apparatus will be denoted by the same reference numerals.

In FIG. 6, reference numeral 30 designates a dialyzing fluid supply unit, which is connected to individual consoles for patients subject to dialysis through motor 31, motor 32, and motor 33. The dialyzing fluid supply unit 30 is provided with an RO water making apparatus 48 having a basic structure including a reverse osmotic membrane (not shown) in a normal dialysis treatment condition. RO water made by the RO water making apparatus 48 is stored in an RO water tank 49 of a predetermined volume. A control box 55, internally having a predetermined dialytic treatment program, actuates an electromagnetic valve 52 and, in turn, a pump 50 actuated thereby, whereby the RO water is supplied with necessity to an RO water inlet 100 of the dialyzing fluid supply unit 30 to be used in the dialytic treatment.

In this dialyzing apparatus, the washing and disinfecting apparatus for dialyzer according to the present embodiment is characterized by having a device 40 for making the electrolytic acid water (AQUA OXYWATER). In this embodiment the device 40 for making the electrolytic acid water is an electrolytic acid water maker (trade name: OXYLYZER OXC-10M) available from Miura Denshi K.K. The electrolytic acid water maker 40 has the anode and the cathode (which are not shown) connected to single-phase 100 V (1A). The acid water maker 40 is comprised of an electrolytic cylinder (not shown) having a so-called diaphragmed structure wherein a diaphragm (not shown) partitions the inside thereof between the anode and the cathode. In the above arrangement, an acid water having an arbitrary value of pH and an arbitrary oxidation-reduction potential may be produced on the anode side by adjusting a voltage applied, an electric current, the time for the treatment, and electrolytic dissociability of the treating water.

The washing and disinfecting apparatus for artificial dialyzer in the present embodiment has a pre-treatment adjuster 39, which is arranged in such a manner that the RO water is supplied thereto as a raw water, salt is dissolved in the RO water, and a saline water is supplied in a predetermined concentration to the above electrolyzing cylinder (not shown) by an adding pump (not shown) built inside the electrolytic acid water maker 40. In the drawing, reference numeral 41 denotes a saline water maker, and 42 an adjuster valve, which is made open to supply the RO water when the water level in an adjuster tank 60 of the above saline water maker 41 becomes below a predetermined level or which is closed to stop supply of the RO water when the water level becomes higher than a predetermined level. This arrangement enables to keep the saline water supplied to the adding pump in the electrolytic acid water maker 40 in a predetermined concentration (20% to 23%), thereby in turn controlling the treating water electrolyzed to a predetermined concentration.

The diaphragmed, electrolyzing cylinder employed in the present embodiment is constructed in such an arrangement that the saline water is pre-treated in the concentration of 20 to 30%, the saline water is supplied to the adding pump, the adding pump supplies the saline water in the concentration of 500ppm to 1000 ppm to the electrolyzing cylinder, and the electrolyzing cylinder electrolytically treats the saline water to produce an acid water.

Electrolysis is carried out under the above conditions. The acid water (AQUA OXYWATER) is made on the anode side of the electrolyzing cylinder forming the electrolytic acid water maker 40 and is stored in an AQUA OXYWATER reservoir 43. The acid water thus stored is supplied with necessity to the disinfectant inlet 21 of the dialyzing fluid supply unit 30 by an electromagnetic valve 47 and a pump 46 actuated thereby.

In the electrolytic acid water maker 40 using the diaphragmed, electrolyzing cylinder in the present embodiment, the acid water made on the anode side after electrolysis is an electrolytic acid water having such properties that pH is between 3.2 and 2.0 both inclusive and the oxidation-reduction potential is at least 870 mV.

For washing and disinfecting the dialyzing apparatus, the electrolytic acid water (AQUA OXYWATER) having the above properties is supplied to the dialyzing fluid supply unit 30 in accordance with the control by the control box 55 having the built-in washing and disinfecting program preliminarily stored, thereby washing and disinfecting the artificial dialyzing apparatus according to the predetermined program. This control program operates the apparatus as follows: for example, during the dialysis treatment, as described previously, the electromagnetic valve 47 is closed to stop the pump 46 while the electromagnetic valve 52 is opened to supply the RO water from the RO water tank 49 to the dialyzing fluid supply unit 30 so as to effect the dialysis treatment; and, during washing and disinfecting of dialyzer, the electromagnetic valve 47 is opened to operate the pump 46, while the electromagnetic valve 52 is closed to supply the AQUA OXYWATER from the AQUA OXYWATER reservoir 43 to the dialyzing fluid supply unit 30 as controlling the RO water not to be supplied from the RO water tank 49 to the dialyzing fluid supply unit 30, thus washing and disinfecting the dialyzing apparatus.

The above control by the control box 55 can automatically be operated with step signals preliminarily stored therein. In addition to it, the apparatus is also arranged so as to enable manual operation through manual buttons (not shown) as occasion demands. During the manual operation an operation to input the medical fluid into the apparatus may be timer-set through a timer (not shown), and after end of timer the control is set so as to automatically return to the operating state.

In some cases, the apparatus may be arranged so as to permit necessary manual operation by manually opening and closing manual valves (having no reference numerals) shown in the drawing instead of the control by these electromagnetic valves 47, 52.

In the drawing reference numerals 44, 45 denote overflow valves provided inside the AQUA OXYWATER reservoir 43, which are arranged as follows. When the reservoir 43 is filled with the water, the valve 44 operates to stop the operation of the electrolytic acid water maker 40, whereas when the reservoir 43 becomes vacant, the valve 45 operates to stop the pump 46.

In the drawing thick solid lines represent a pipe line system, thin solid lines an electric system, and dashed lines a control system. In this embodiment pipe lines are those having apertures of ½ or ¾ properly selected, a material for the pipe lines is a rigid polyvinyl chloride (HIPVC), and there are no metal parts used for thread portions throughout the entire system. This comes from the viewpoint of anti-corrosion.

In the present embodiment the electrolytic acid water maker 40 employs the apparatus having the diaphragm (not shown) partitioning the space between the anode and the cathode (which are not shown), and the acid water is thus taken out from the anode side. It is noted that the invention is not intended to be limited to this type of apparatus, but the apparatus may be constructed as a so-called "diaphragmless" apparatus without giving a diaphragm. Namely, the apparatus may be constructed either with or without the diaphragm as long as it can make the electrolytic acid water. It is, however, noted in view of the purpose of washing and disinfecting the dialyzing apparatus that, in the case of using the diaphragmed, electrolyzing cylinder, the acid water obtained from the anode side must be the electrolytic acid water having the properties of the pH value of from 3.2 to 2.0 both inclusive and the oxidation-reduction potential of not less than 870 mV, or else it cannot demonstrate a distinct effect for washing and disinfecting the dialyzing apparatus.

Similarly, the inventor found that when a so-called diaphragm-less electrolytic cylinder, not having the diaphragm between the electrodes disposed in the electrolytic cylinder, was used, the acid water obtained from the anode side must be the electrolytic acid water having the properties of the pH value of from 6.5 to 2.0 both inclusive and the oxidation-reduction potential of not less than 800 mV, or else it could not demonstrate a distinct effect for washing and disinfecting the dialyzing apparatus. Therefore, sufficient attention must be paid to the properties of the acid water obtained depending upon the type of the electrolytic cylinder used.

The present embodiment is constructed in such a manner that the acid water can be obtained by electrolyzing the RO water thus made and that the RO water can also be supplied from the tank 49 to the electrolytic acid water maker 40 whereby the RO water with as little mixture of various germs etc. as possible can be used in making the electrolytic acid water used for washing and disinfecting of dialyzer, thus enhancing the effect of wash and disinfection of dialyzer. For this purpose, the present embodiment has the pre-treatment adjuster 39 arranged to perform such adjustment that the RO water from the RO water tank 49 is used as a raw water, the saline water of the adjusted concentration is added thereto, and then the saline water of a predetermined concentration is supplied to the electrolytic cylinder. Namely, the RO water from the RO water tank 49 is supplied as a treated water adjusted in the predetermined pretreatment concentration to the electrolytic cylinder of the electrolytic acid water maker 40 by the saline water maker 41 and concentration adjuster valve 42, and the saline water is subjected to the specific electrolysis to obtain the electrolytic acid water.

Incidentally, during artificial dialysis, the dialyzing fluid supply unit 30 is arranged to supply the dialyzing fluid at temperature in the range of about 35° C. to 38° C. matching the temperatures of human body to the individual consoles. Thus, the RO water in the RO water tank 43 is also heated to the temperature in the range of about 35° C. to 42° C.

Then, introduction of the RO water in the heated state to the pre-treatment adjuster 39 would result in providing a good environment for the propagation of bacteria because the RO water is obtained by eliminating the chlorine component, different from the use of tap water, and the RO water has the moderate temperature and moderate salt content. Particularly, an increase of Gram-negative bacteria such as Pseudomonas aeruginosa is outstanding under the environment of the present embodiment with addition of salt. When the increased bacteria are supplied to the electrolytic cylinder, the bacteria themselves momentarily die because of the voltage or electric current applied, but there is a risk that dead bodies thereof (endotoxins) come to contact the blood through the dialyzer as they are.

Since alive or increasing bacteria sometimes discharge strong toxins (exotoxins), there is another risk that these toxins (exotoxins) come to contact the blood through the dialyzer as they are. Although it was intended in wash and disinfection of dialyzer that the RO water was used as a raw water for the electrolytic acid water in order to perform wash and disinfection in a state of as little mixture of various germs etc. as possible in the electrolytic acid water used, the result was opposite to that as expected because of the necessity to use the RO water heated.

Hence, the following experiments were carried out to find out a countermeasure for suppressing the increase of bacteria in the pre-treatment adjuster 39.

(Experiment 1)

Under the same environmental conditions as inside the pre-treatment adjuster 39, Pseudomonas aeruginosa was added to the RO water and 5 kg of salt, and an increase of Pseudomonas aeruginosa was checked after kept at 37° C. for 48 hours.

(Experiment 2)

Similarly, Pseudomonas aeruginosa was added to the RO water and 5 kg of salt, and the two electrodes of 90 cm$^2$ were placed at an interval of 3 mm under the level of the solution. A voltage of 5 V was applied between these electrodes to let a direct current of 150 mA flow for 5 minutes, and the current was stopped for 20 minutes. After that, the polarity was reversed, and then the direct current was let to flow for the same period and at the same interval. Then an increase of Pseudomonas aeruginosa was checked similarly after kept at 37° C. for 48 hours in this manner.

(Experiment 3)

Similarly, Pseudomonas aeruginosa was added to the RO water and 5 kg of salt, and an ultraviolet lamp was set under the level of the solution. The solution was placed under irradiation of ultraviolet light at 37° C. for 48 hours. After the irradiation an increase of Pseudomonas aeruginosa was checked.

(Experiment 4)

The electrolytic acid water (which is an acid water obtained by adding salt to the RO water not heated) itself was maintained in the state of 37° C., and an increase of Pseudomonas aeruginosa was checked after that.

The results showed that the number of Pseudomonas aeruginosa checked was approximately $10^4$ in Experiment 1 while no Pseudomonas aeruginosa was observed in Experiment 2 to Experiment 4.

Figure 7:
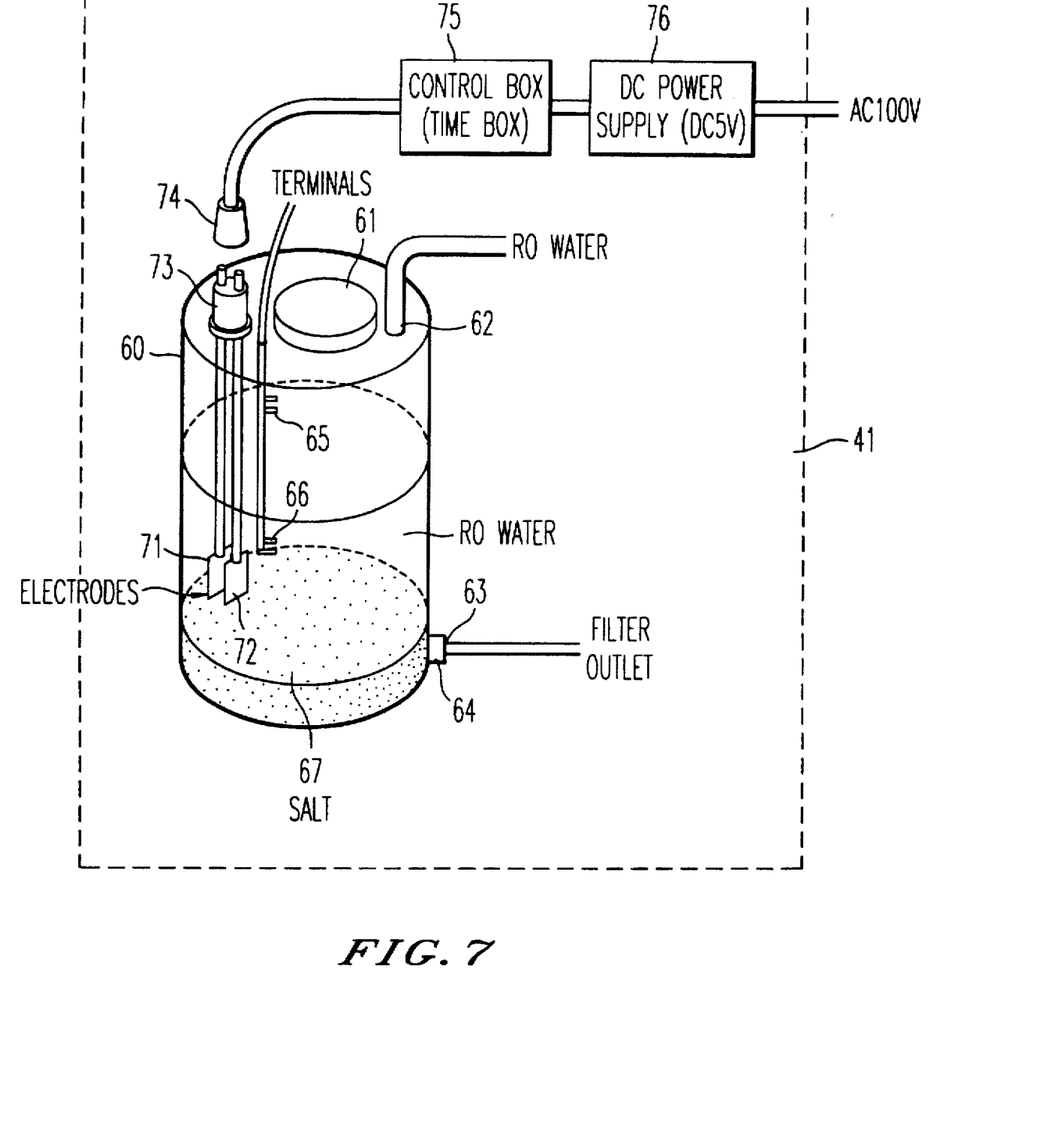
FIG. 7 is a schematic drawing to show a basic setup of a pre-treatment adjuster used in supplying the RO water to the electrolytic cylinder.

In view of the above results the inventor devised the pre-treatment adjuster 39 as shown in FIG. 7. This pre-treatment adjuster 39 was used to control the concentration of the saline water in the following manner. The RO water in a heated state was supplied as a raw water to the pre-treatment adjuster 39, and a saline water of an adjusted concentration was added thereto so that a saline water of a predetermined concentration could be supplied to the electrolytic cylinder.

FIG. 7 is a schematic drawing to show the basic setup of the pre-treatment adjuster 39. In the drawing, reference numeral 60 designates an adjuster tank, 61 a salt inlet, and 62 an RO water supply port, which is connected to the RO water maker 48 and through which the RO water made thereby is supplied. Numeral 63 represents an outlet of the adjusted water (saline water) obtained by adding salt to the RO water, which is connected to the electrolytic cylinder through the adding pump (not shown).

Further, numeral 64 stands for a filter provided in the outlet 63, and 65, 66 for float switches for controlling the level of solution in the adjuster tank 60, wherein 65 is an upper switch and 66 is a lower switch. Numeral 67 indicates the salt put in the tank.

Numerals 71, 72 represent the electrodes of 90 cm$^2$ disposed at the interval of 3 mm inside the adjuster tank 60. These electrodes 71, 72 are connected to the control box 75 and DC power supply 76 (DC 5V) through terminals 73, 74. The control box 75 performs such control that the voltage 5 V is applied between these electrodes 71, 72 to let the direct current of 150 mA flow for 5 minutes and then the current is stopped for 20 minutes and that thereafter the polarity is reversed and the current is let to flow for the same period and at the same interval.

The pretreatment adjuster 39 is constructed in such a manner that salt 67 is preliminarily put through the salt inlet 61 into the tank and the RO water is supplied through the RO water supply port 62, thereby making the saline water containing the RO water. On this occasion, the concentration of the saline water to be made is adjusted by controlling a supply amount of the RO water so that the saline water may have the concentration in the range of approximately 20 to 23% at the point of passage through the filter 64. Therefore, various germs will not propagate in the adjuster tank 60 even after long-term storage in the state where salt is added to the RO water kept at constant temperature.

Then, the saline water of the concentration of approximately 20% to 23% is discharged through the outlet 63 and is supplied to the electrolytic cylinder of the electrolytic acid water maker 40 through the adding pump (not shown). On the other hand, the RO water from the RO water maker 48 is also supplied directly to the electrolytic cylinder of the electrolytic acid water maker 40, as shown in FIG. 6. This RO water is mixed with the saline water containing the RO water in the concentration of approximately 20% to 23% from the pre-treatment adjuster 39 immediately before supply to the electrolytic cylinder, so that the adding pump controls the flow rate of supply so as to achieve the concentration of salt of 0.05% to 0.1% (500 ppm to 1000 ppm) and the electric conductivity of 1000 to 2000 µS/m.

Namely, the saline water supplied to the electrolytic cylinder is diluted with the RO water by controlling the speed of the adding pump having a constant stroke, so that the saline water is supplied in the concentration of 500 ppm to 1000 ppm to the electrolytic cylinder. Thus, the electrolytic cylinder is always filled with the water obtained by dissolving the salt in the RO water in the concentration of 500 ppm to 1000 ppm.

As a result, electrolysis will result in obtaining an acid water of pH 2.7 (when the supply saline water is in 500 ppm) to pH 2.4 (when the saline water is in 1000 ppm).

The present embodiment is arranged so that the electrodes 71, 72 are disposed inside the adjuster tank 60 of the pre-treatment adjuster 39 and that the direct current is let to flow between the electrodes 71, 72 whereby various germs may be prevented from propagating inside the adjuster tank 60, but another arrangement for preventing the propagation of various germs may also be employed in such a setup that the adjuster tank 60 is made of a transparent body so as to permit ultraviolet rays to be radiated from the outside of the tank 60 and that an ultraviolet lamp for emitting ultraviolet rays is disposed outside the tank 60 in order to irradiate the RO water inside.

The inventor of the present invention has been developing the method and apparatus of the type wherein AQUA OXYWATER was input through the disinfectant inlet 21 for introduction of disinfectant to the dialyzing apparatus, as explained in the previous embodiments. However, inadequate wash and disinfection could result, if AQUA OXYWATER were input through the disinfectant inlet of the dialyzing apparatus thereinto. Describing it in more detail, the washing program normally employed is arranged to wash the dialyzing apparatus of this type with a solution in which 3.5% to 0.35% of sodium hypochlorite solution, which is a disinfectant introduced through the inlet 21, is diluted with the RO water simultaneously introduced therethrough at a dilution ratio of about 35. In the above description, 3.5% sodium hypochlorite solution is used to wash and, disinfect the dialyzing apparatus within a short time period, normally for about two hours, and 0.35% of sodium hypochlorite solution is used to wash and disinfect the dialyzing apparatus for about ten hours, normally from the end of dialysis treatment to a next morning. Further, the sodium hypochlorite solution is normally diluted at the dilution ratio of about 35 in the normal wash and disinfection cases, though it depends upon the type of dialyzer and the concentration of the sodium hypochlorite solution used. Therefore, because wash and disinfection of dialyzer is carried out with the diluted solution of AQUA OXYWATER, wash and disinfection could be inadequate in some cases.

Under the above circumstances, the inventor of the present invention found that if the AQUA OXYWATER was input through the clean water inlet (the RO water inlet) 100, the solution-A inlet 101, or the solution-B inlet 102, where no dilution was effected, an especially excellent effect could be achieved for washing and disinfecting the dialyzing apparatus, and also found that employment of the washing and disinfecting method of this type could enable to achieve easy wash and disinfection of dialyzer without changing the wash and disinfection program preliminarily set in the dialyzing apparatus.

Since the sodium hypochlorite solution used as a disinfectant is harmful to the human body, it is intended to wash and disinfect the portions in contact with the blood with the solution of a concentration as low as possible. Since the present invention uses the AQUA OXYWATER which is fundamentally harmless to the human body and which becomes not to show strong acidity and oxidation-reduction potential, no negative effect will be caused in the use of AQUA OXYWATER at the portions in contact with the blood.

Thus, a higher effect to wash and disinfect the dialyzing apparatus can be attainted by inputting AQUA OXYWATER through the clean water inlet (RO water inlet) 100, the solution-A inlet 101, or the solution-B inlet 102 of the dialyzing apparatus thereto. This arrangement requires no change of the washing program at all, and permits AQUA OXYWATER readily to be input. In addition, the input of AQUA OXYWATER into either one of these inlets will cause no negative effect on the dialysis treatment at all. Consequently, a much more excellent washing and disinfecting effect can be attained by inputting AQUA OXYWATER through either one of these clean water inlet (RO water inlet.) 100, solution-A inlet 101, and solution-B inlet 102 rather than by inputting it through the disinfectant inlet 21 of the dialyzing apparatus. Therefore, the inventor thus established the method for washing and disinfecting the dialyzing apparatus.

The conventional methods and apparatus were unable to completely eliminate bacteria, fungi, viruses, etc. inside (the dialyzing apparatus even by the long-term cleaning and disinfecting operation for 1 to 3 hours with the disinfectant mainly containing a sodium hypochlorite solution or an acetic acid solution in the period between dialysis treatments, whereas the present invention realized the method using the electrolytic acid water for wash and disinfection of the dialyzing apparatus to almost completely eliminate these germs, thus presenting the very excellent effect to perfectly stop occurrence of infectious disease in dialysis.

Further, the conventional methods and apparatus had the problems that a nutrition source such as calcium included in a fine amount in the dialyzing fluid or water per se was deposited on the inside of the pipe lines etc. to allow new various germs etc. to propagate there, dead bodies (endotoxins) of bacteria per se remained inside the pipes then to be circulated with the blood into a patient's body, and they could cause the patient to have cryptogenic fervescence after the dialysis treatment, but use of the electrolytic acid water for washing of the dialyzing apparatus according to the present invention can decompose and eliminate the deposits inside the pipes so as to easily remove the endotoxins etc. inside the fluid, thus permitting safe dialysis.

Additionally, the method of disinfection using sodium hypochlorite or the like could cause negative effects on the human body and on the other environments due to the residual components after long-term use, whereas the use of the electrolytic acid water has the excellent effect to suppress such negative effects because the electrolytic acid water has a strong disinfecting effect because of its strong acidity and high oxidation-reduction potential but the acidity effect disappears after left for a while.

What is claimed is:

1. A washing and disinfecting method for artificial dialyzer using an electrolytic acid water, comprising:
   supplying an acid water obtained by electrolysis to an artificial dialyzer said acid water having a pH in the range of 6.5 to 2.0 both inclusive and an oxidation-reduction potential of at least 800 mV; and
   circulating or retaining said acid water for a predetermined period in tanks, pipe lines, and a hemodialyzing portion constituting the artificial dialyzer, thereby substantially eliminating bacteria, fungi, and viruses from the the artificial dialyzer.

2. The method according to claim 1, wherein an inorganic additive is dissolved in a water to obtain a solution, said solution is supplied to an electrolytic cell having an anode and a cathode and partitioned by a diaphragm between said anode and cathode, a direct current of a predetermined voltage is applied to said two electrodes to obtain an acid water with pH being in the range of 3.2 to 2.0 both inclusive and an oxidation-reduction potential being at least 870 mV from the anode side, and said acid water is supplied to the artificial dialyzer to wash and disinfect the inside of said artificial dialyzer.

3. The method according to claim 1, wherein an inorganic additive is dissolved in a water to obtain a solution, said solution is supplied to an electrolytic cell having an anode and a cathode but having no diaphragm, a direct current of a predetermined voltage is applied to the electrodes to obtain an acid water, wherein said acid water is supplied to the artificial dialyzer to wash and disinfect the inside of the artificial dialyzer.

4. The method according to claim 3, wherein said acid water is an acid water obtained by supplying a solution in which an inorganic additive and an inorganic acid are dissolved in a water, to the electrolytic cell.

5. The method according to claim 1, wherein an inorganic acid or/and a halide is mixed in the acid water obtained from the anode side, thus obtaining a mixture liquid showing pH in the range of 5.0 to 2.0 both inclusive, and the mixture solution thus obtained is supplied to the artificial dialyzer to wash and disinfect the inside of the artificial dialyzer.

6. The method according to claim 2, wherein said acid water is an acid water containing at least 5 ppm of an oxidized or chlorinated substance.

7. The method according to claim 6, wherein the oxidized or chlorinated substance is selected from the group consisting of $Cl_2$, $HOCl$, and $O_3$.

8. The method according to claim 2, wherein the water is tap water or water passing through a reverse osmotic membrane.

9. A method for decomposing and eliminating a deposit containing calcium, comprising:
   supplying an acid water obtained by electrolysis to an artificial dialyzer said acid water having a pH in the range of 6.5 to 2.0 both inclusive and an oxidation-reduction potential of at least 800 mV; and
   circulating or retaining said acid water for a predetermined period in tanks, pipe lines, and a hemodialyzing portion constituting the artificial dialyzer, thereby decomposing and eliminating a deposit containing calcium adhering to said tanks, pipe lines, and hemodialyzing portion inside the artificial dialyzer.

10. A method for eliminating endotoxins (dead bodies of bacteria), comprising:

supplying an acid water obtained by electrolysis to an artificial dialyzer said acid water having a pH in the range of 6.5 to 2.0 both inclusive and oxidation-reduction potential of at least 800 mV; and circulating or retaining said acid water for a predetermined period in tanks, pipe lines, and a hemodialyzing portion constituting the artificial dialyzer, thereby eliminating endotoxins from the inside of the artificial dialyzer.

11. A washing and disinfecting method for artificial dialyzer, comprising:

supplying an alkaline water having a pH of at least 9.0 and obtained by electrolysis to an artificial dialyzer;

circulating or retaining said alkaline water for a predetermined period in tanks, pipe lines, and a hemodialyzing portion constituting the artificial dialyzer;

thereafter supplying an acid water obtained by said electrolysis to said artificial dialyzer said acid water having a pH in the range of 6.5 to 2.0 both inclusive and an oxidation-reduction potential of at least 800 mV; and circulating or retaining said acid water for a predetermined period in the tanks, pipe lines, and hemodialyzing portion constituting the artificial dialyzer, thereby substantially eliminating bacteria, fungi, and viruses from the artificial dialyzer.

12. The method according to claim 11, wherein said acid water is an acid water containing at least 5 ppm of an oxidized or chlorinated substance.

13. The method according to claim 12, wherein the oxidized or chlorinated substance is selected from the group consisting of $Cl_2$, $HOCl$, and $O_3$.

* * * * *